United States Patent [19]

Standke et al.

[11] Patent Number: 5,210,334
[45] Date of Patent: May 11, 1993

[54] PROCESS FOR THE PREPARATION OF ALKALINE EARTH METAL ALKYLATES HAVING A SPHERICAL PARTICLE FORM

[75] Inventors: Burkhart Standke; Hartwig Rauleder, both of Rheinfelden, Fed. Rep. of Germany; Harald-Jürgen Biangardi, Chesterfield, Mo.; Hans-Joachim Kötzsch, Rheinfelden, Fed. Rep. of Germany

[73] Assignee: Huels Aktiengesellschaft, Marl, Fed. Rep. of Germany

[21] Appl. No.: 807,271

[22] Filed: Dec. 13, 1991

[30] Foreign Application Priority Data

Dec. 17, 1990 [DE] Fed. Rep. of Germany ....... 4040252

[51] Int. Cl.$^5$ ............................................. C07C 31/30
[52] U.S. Cl. ....................................................... 568/851
[58] Field of Search ......................................... 568/851

[56] References Cited

U.S. PATENT DOCUMENTS 4,851,208   7/1989   Duranel et al. ..................... 568/851

OTHER PUBLICATIONS

Webster's Third International New Dictionary, Merriam, 1963, p. 336.

Webster's II, Houghton-Mifflin 1984, p. 557.

Primary Examiner—Marianne M. Cintins
Assistant Examiner—Rebecca Cook
Attorney, Agent, or Firm—Felfe & Lynch

[57] ABSTRACT

Alkaline earth metal alkylates having a spherical particle habit are prepared by dissolving an alkaline earth metal alkylate in a solvent, adding a second solvent which dissolves the alkaline earth metal alkylate only with difficulty or does not dissolve it at all, but which is homogeneously miscible with the solution of the alkaline earth metal alkylate in the first solvent, removing the first solvent and then removing the second solvent. The particle size can be controlled by means of the shear gradient during the precipitation or by the use of emulsion stabilizers. Emulsion stabilization leads to particles in the size range 0.5 to 20 $\mu$m with a particularly narrow particle size distribution. Catalysts for polyolefin synthesis can be prepared on the basis of magnesium alkylates prepared by the process according to the invention. The polymer is advantageous with respect to particle habit and particle size distribution, compared with the prior art. A narrower particle size distribution, and thus a reduction in undesired oversize and undersized particles, and a smoother surface structure are achieved.

7 Claims, No Drawings

PROCESS FOR THE PREPARATION OF ALKALINE EARTH METAL ALKYLATES HAVING A SPHERICAL PARTICLE FORM

FIELD OF THE INVENTION

This invention relates to a novel process for the preparation of alkaline earth metal alkylates having a spherical or spheroid particle form in the size range from 1 to 500 μm by precipitation from homogeneous solution.

BACKGROUND OF THE INVENTION

In the industrial synthesis of alkaline earth metal alkylates, for example from alkaline earth metal filings and an alkanol, the corresponding alkylate is obtained with an irregular grain structure. However, many applications demand specially fabricated products; for example, spherical particles of relatively monomodal particle size distribution. Active catalyst support substances based on magnesium ethylate having a spherical particle habit and an average particle diameter of 10-20 μm having proved particularly suitable for the polyolefin synthesis using Ziegler catalysts (see Published European Applications 0 236 082 and 0 159 150). The processes for the preparation of spherical or spheroid alkaline earth metal alkylates prove to be expensive industrially; it is true that spray-drying of carbonized ethanolic magnesium ethylate solutions with subsequent decarbonization by heat treatment in a stream of nitrogen (Published European Application 0 236 082) yields a magnesium ethylate powder having an approximately spherical particle form, but this powder has a highly structured surface, resulting from the collapse of hollow spheres formed during the spray process (raisin structure). Since the spray-drying must be carried out under inert gas conditions, the process is very expensive industrially if the solvent is to be recycled from the large stream of inert gas required for the spray-drying. Particle sizes of <10 μm are not accessible in industrial spray installations using this process nor by precipitation reactions in accordance with Published European Application 0 214 891 in complex solvent mixtures.

DESCRIPTION OF THE INVENTION

According to the present invention, alkaline earth metal alkylates of the formula I below having a spherical or spheroid particle form in the particle size range of 0.5-500 μm can be prepared on the basis of a homogeneous precipitation reaction.

$$M(OR^1)_a(OR^2)_b(CO_2)_x \quad (I)$$

M = magnesium, calcium, strontium or barium, preferably magnesium;

$R^1$ and $R^2$ = identical or different alkyl radicals of 1 to 8, preferably 1 to 6, carbon atoms, $a+b=2$, $0 \leq a \leq 2$, $0 \leq b \leq 2$, and $0 \leq x \leq 2$.

The process is based on the following general procedure:

1. Dissolving an alkaline earth metal alkylate in a suitable solvent $L_1$, if appropriate by means of the additional action of $CO_2$ as solubilizing agent.
2. Mixing of the homogeneous solution obtained in 1. with a solvent $L_2$, in which the pure alkaline earth metal alkylate or a compound formed from the alkaline earth metal alkylate and the solubilizing agent is insoluble or only sparingly soluble, but which is miscible with the solvent $L_1$ used in 1., to dissolve the alkaline earth metal alkylate, and which permits separation of the solvents $L_1$ and $L_2$ used in 1. and 2. by distillation in such a way that, after removal of the solvent $L_1$, used in 1., from the homogeneous mixture obtained in 2., by distillation, a precipitation product having the formula I remains as a dispersion in solvent $L_2$.
3. Removal of $L_1$ by distillation. During this operation, particles having the formula I are formed as a dispersion in $L_2$.
4. Separation of the precipitation product from $L_2$: a) filtration and subsequent drying of the filter cake; b) removal of $L_2$ from the precipitation product by distillation.

The control of the particle size may be effected in process step 3:

a) Control of the particle size via the shear gradient: at a low shear gradient (for example, use of paddle stirrers at a low speed of revolution) roughly spherical particles in the size range of up to 500 μm are obtained. By using "high shear" dispersion equipment working on the rotor/stator principle (for example Ultra Turrax, Jahnke und Kunkel) the particle size can be reduced down to 2-3 μm. Depending on the shear gradient (dependent on dispersion equipment and the circumferential speed set), intermediate sizes are also obtainable.

b) Droplet stabilization by the use of emulsifying aids: since, before the formation of hard particles, an emulsion, consisting of $L_2$ as continuous phase and a homogeneous, viscous phase, composed of $L_1$, $L_2$ and the alkaline earth metal compound of formula I as emulsified phase, is at first formed in process step 3 upon removal of $L_1$ from the homogeneous reaction mixture by distillation, the droplets of the emulsified phase produced by the shear gradient can be stabilized by means of suitable emulsion stabilizers, which settle at the interface between the continuous and emulsified phase. The stabilization of the emulsion initially formed in process step 3, by means of auxiliaries, promotes the preparation of, in particular, small particles (diameter 0.5-20 μm) having a virtually monomodal particle size distribution, that is to say particles having a narrow distribution of the particle sizes and a spherical particle form. A suitable emulsion stabilizer in the process described is, in particular, pyrogenic silica (for example Cab-O-Sil TS 720, Cab-O-Sil M5). Pyrogenic silica meets the requirement for a suitable solid emulsion stabilizer: adequate dispersivity (primary particle sizes in the range of a few nanometers, readily dispersible in $L_1$ and $L_2$) and incomplete wettability of the solid (silica) by the inner liquid phase (emulsified phase) consisting of the alkaline earth metal compound having the formula I, in the solvents $L_1$ and $L_2$.

Investigations in the transmission electron microscope: investigations on ultrathin sections (150 nm thick) show that precipitated particles stabilized in this way are $SiO_2$-coated alkaline earth metal alkylate spheres. The thickness of the silica coating is 40-50 nm. By dispersing particles of this type in an inert solvent and treating the dispersion with ultrasonic sound or "high shear" dispersers, the silica coating can be substantially detached from the particle surface. The separation of alkaline earth metal alkylate and silica is carried out subsequently via sedimentation.

By means of interaction of process steps 1 to 3, the object of preparing spherical or spheroid particles of alkaline earth metal alkylates having the formula I is achieved. The term "spherical" means a spherical form, while "spheroid" means an approximately spherical grain habit.

The use of a controlled, continuously acting shear gradient in process step 3 leads to continuous droplet dispersion within the emulsion formed as an intermediate, in particular of droplets which exceed a certain size because of coalescence processes. The size of the resulting emulsion droplets is, as a first approximation, inversely proportional to the shear gradient (a high shear gradient produces small droplets). Low shear gradients are achieved with numerous stirrers of conventional construction, while high shear forces are achievable, in particular, by means of rotor/stator constructions having an external cylindrical stator and an adjustable rotor of arbitrary design, the circumferential speeds of which should be between 5 and 25 m/s, preferably between 10 and 21 m/s.

Since the viscosity of the inner phase rises very sharply in the course of the removal of the solvent $L_1$ by distillation (in the case of complete removal of $L_1$, the inner phase is to be regarded as a solid), coalescence processes no longer play a role at the end of process step 2, so that the separation of the solid from the solvent $L_2$ can take place without the action of a shear gradient by filtration or by removal of $L_2$ by distillation.

In the case of the preparation of small particles in the range 0.5 to 20 $\mu$m, the continuously acting high shear gradient can be dispensed with if suitable emulsion stabilizers are used which prevent a coalescence of the emulsion droplets formed as a result of shear action. Compact, spherical particles having a virtually monomodal particle size distribution are obtained reproducibly in a simple way.

The temperatures of the process do not have an essential influence on the form and size of the particles. Advantageously, however, the solution from process step 1 and its mixture with $L_2$ are prepared at elevated temperature, insofar as the particular solution then has a relatively high concentration. The temperature during the distillation depends on the boiling point of the particular solvent, which can be lowered in a conventional manner by means of reduced pressure.

"Alkaline earth metal" very preferably means Mg and optionally also Ca, Sr or Ba.

The solvents $L_1$ are polar protic solvents, in particular alkanols having 1 to 6 carbon atoms (straight-chain or branched), preferably methanol, ethanol, propanol or butanol. Mixtures of the said solvents can also be used.

The amount of the solvents $L_1$ depends on the solubility of the alkylate in the solvent $L_1$ or of the carbonized alkylate in the solvent $L_1$, a saturated solution of the alkylate very preferably being used.

The solvents $L_2$ are polar or non-polar aprotic solvents, in particular hydrocarbons (straight-chain, branched, aromatic or mixtures thereof), ethers and tetraalkoxysilanes, and if appropriate also ketones, carboxylic acid esters or alkylalkoxysilanes having a boiling point higher than $L_1$ and a lower solubility of the alkaline earth metal alkylate in $L_2$ than in $L_1$. Mixtures of the solvents $L_2$ mentioned can also be used.

The amount of the solvent $L_2$ can vary within wide limits, since in each case a precipitation occurs to the extent that $L_1$ is removed. Preferably, solids concentrations of y % are used at the end of process step 3; $0 < y \leq 70$, preferably $1 \leq y \leq 10$.

If an alkanol other than that which corresponds to the alkylate radical of the alkaline earth metal alkylate to be dissolved is used to dissolve the alkaline earth metal alkylate, or if solvents which are able to eliminate such alkanols in the course of the reaction—for example carboxylic acid esters, silicates, titanates and the like—are used as $L_1$ or $L_2$, transalkanolization takes place in the alkaline earth metal compound to some extent. Mixed alkylates of the formula I are then isolated.

A basic application of specially fabricated alkaline earth metal alkylates is the use as active catalyst support material in polyolefin synthesis. The formulations for the preparation of highly active catalysts—for example for propene polymerization based on magnesium alkylate as active catalyst support material—are known. Since particle morphology and range of distribution are superior in the case of the process according to the invention compared with the prior art (for example spray-drying of carbonized magnesium alkylate solutions), this has a favorable effect on the properties of the polymer powder. The term "carbonized" as used herein is intended to mean "treated with carbon dioxide." In the case of isotactic propene polymerization, the polymer grain structure is an accurate, but volumetrically magnified, image of the catalyst grain structure. Use of a magnesium ethylate prepared by the process according to the invention as active catalyst support material in isotactic propene polymerization leads to a narrower particle size distribution in the polymer (undesired oversize and undersize particles are reduced) and to a smoother particle surface.

The following examples illustrate the present invention and will enable others skilled in the art to understand it more completely. It should be understood, however, that the invention is not limited solely to the particular examples given below.

EXAMPLE 1

Precipitation from a homogeneous medium using a low shear gradient 1836 g of ethanol and 292 g of magnesium ethylate (standard grain, commercial product from Hüls AG) were introduced into a reactor, fitted with a stirrer, a gas inlet device and a distillation bridge, under a dry nitrogen atmosphere. 194 g of $CO_2$ were passed in over the course of 2 hours, while stirring. A flesh-colored solution of carbonized magnesium ethylate in ethanol was formed. 2829 g of diethylene glycol dimethyl ether were added to this solution. At this point in time a homogeneous solution was present in the reaction vessel. At a sump temperature rising from 86° C. to 130° C., the entire amount of ethanol was distilled off in the course of 2 hours, while stirring with a paddle stirrer. A milky white turbidity (precipitation from homogeneous medium) formed. Under dry nitrogen the precipitate was then filtered off with suction on a G4 sintered crucible and washed several times with acetone. The filtrate consisted of diethylene glycol dimethyl ether. After drying at 90° C. (p<1 mbar), 210 g of product (solid, carbonized magnesium ethylene) were isolated from the filter cake. Particles of 50–200 $\mu$m diameter were obtained. The produce (mixture of magnesium ethylate and carbonized magnesium ethylate) contained about 14% of $CO_2$. The $CO_2$ content could be reduced to below 2% by subjecting it to a heat treatment for 2 hours at 180° C. (p<1 mbar).

EXAMPLE 2

Precipitation from homogeneous medium using a moderate shear gradient 1836 g of ethanol and 292 g of magnesium ethylate (standard grain, commercial product from Hüls AG) were introduced into a stirrer reactor (stirrer=Ultraturrax T50, Jahnke und Kunkel), fitted with a gas inlet device and a distillation bridge, under a dry nitrogen atmosphere. 194 g of $CO_2$ were passed in over the course of 2 hours, while stirring. A flesh-colored solution of carbonized magnesium ethylate in ethanol was formed. 5803 g of xylene were added to the homogeneous solution, while stirring. The ethanol was then distilled off completely in the course of 3 hours at a speed of revolution of the stirrer of 4000 rev/min (maximum sump temperature 90° C., minimum pressure 200 mbar). A dispersion formed, which was freed from xylene in a rotary evaporator. The residual, flowable white powder was then dried at a temperature of 180° C. (under a pressure of less than 1 mbar) for 2 hours in a rotary evaporator. 233 g of magnesium ethylate ($CO_2$ content<2%) were isolated. Particle size analysis showed rounded particles having an average diameter of about 20 μm.

EXAMPLE 3

Precipitation from homogeneous medium using a high shear gradient

The test procedure corresponded to that of Example 2, except that the speed of revolution of the stirrer was switched to maximum power (10,000 rev/min).

After drying in a rotary evaporator, 230 g of pourable magnesium ethylate ($CO_2$ content<2%) were isolated.

Particle size analysis showed rounded particles having an average diameter of about 3 μm.

EXAMPLE 4

Precipitation from homogeneous medium, particle stabilization by means of hydrophobic pyrogenic silica 1836 g of ethanol and 292 g of magnesium ethylate (standard grain, commercial product from Hüls AG) were introduced into a reactor, fitted with a stirrer, a gas inlet device and a distillation bridge, under a dry nitrogen atmosphere. 194 g of $CO_2$ were passed in over the course of 2 hours, while stirring. A flesh-colored solution of carbonized magnesium ethylate in ethanol formed. In a second flask, 173 g of pyrogenic silica which had been rendered hydrophobic (Cab-O-Sil TS 720) were dispersed in 5803 g of xylene, using an Ultraturrax (T50, Jahnke u. Kunkel) to give a slightly opalescent suspension. The silica dispersion was then introduced into the solution of carbonized magnesium ethylate, while stirring. All of the ethanol was distilled off in the course of 6 hours under normal pressure (maximum sump temperature 125° C.). During this period the liquid, which initially was only slightly opalescent, became distinctly turbid. The resulting dispersion was brought to complete dryness in a rotary evaporator, xylene being separated ($T_{max\cdot}$=180° C., $P_{min\cdot}$<1 mbar). 380 g of a pourable, finely divided magnesium ethylate powder having a $CO_2$ content of <2% were formed. Analysis by light microscopy and electron microscope showed that the precipitation product formed consisted of spherical magnesium ethylate particles measuring on average about 5 μm which had an approximately 50 nm thick silica coating.

EXAMPLE 5

Precipitation from homogeneous medium, particle stabilization by means of hydrophillic pyrogenic silica 1836 g of ethanol and 292 g of magnesium ethylate (standard grain commercial product from Hüls AG) were introduced into a reactor, fitted with a stirrer, a gas inlet device and a distillation bridge, under a dry nitrogen atmosphere. 194 g of $CO_2$ were passed in over the course of 2 hours, while stirring. A flesh-colored solution of carbonized magnesium ethylate in ethanol was formed.

In a second flask, 214 g of pyrogenic silica (Cab-O-Sil M5) were dispersed in 3571 g of n-heptane using an Ultraturrax stirrer (T50, Jahnke u. Kunkel) to give a slightly opalescent suspension. The silica dispersion was then introduced into the solution of carbonized magnesium ethylate, while stirring. All of the ethanol was distilled off (as an azeotrope with n-heptane) in the course of 3 hours under normal pressure (sump temperature rising from 83° C. to 89° C.). During this period the liquid, which initially was only slightly opalescent, became distinctly turbid. The resulting dispersion was brought to complete dryness in a rotary evaporator, the residual n-heptane being separated off $T_{mac\cdot}$=180° C., $P_{min\cdot}$<1 mbar). 380 g of a pourable, finely divided magnesium ethylate powder having a $CO_2$ content of <2% were formed. Analysis by light microscopy and electron microscope showed that the precipitated product which had formed consisted of spherical, silica-coated magnesium ethylate particles measuring about 1 μm.

EXAMPLE 6

Precipitation of magnesium ethylate/methylate mixed alkylates 763.6 g of tetraethoxysilane were added to 500 ml of a magnesium methylate solution (prepared by dissolving 18 g of magnesium metal in 500 ml of methanol) in a heatable 2-liter flask fitted with an Ultraturrax T50 stirrer (Jahnke und Kunkel, stirring rate 4000 rev/min) and a 30 cm distillation column. A mixture of methanol, ethanol, tetraethoxysilane, triethoxymethoxysilane, diethoxydimethoxysilane, ethoxytrimethoxysilane and tetramethoxysilane (composition—GC percentage area: 37% methanol, 40% ethanol, 23% silane) was then distilled off while the sump temperature rose from room temperature to 150° C. The residual dispersion was transferred under a protective gas into the flask of a rotary evaporator and concentrated to dryness under a pressure falling from ambient pressure to <1 mbar and at a maximum temperature of 170° C. 38 g of a pourable magnesium alkylate powder of the formula $MG(OC_2H_5)_{1.22}(CH_3)_{0.78}$ having an average particle size of about 10 μm (evaluation by light microscope) were obtained.

EXAMPLE 7

Precipitation of magnesium methylate 750 g of tetramethoxysilane were added to 500 ml of a magnesium methylate solution (prepared by dissolving 18 g of magnesium metal in 500 ml of methanol) in a heatable 2-liter flask fitted with a paddle stirrer and a 30 cm distillation column. A mixture of methanol and tetramethoxysilane (composition—GC percentage area:

55% methanol, 45% tetramethoxysilane) was then distilled off while the sump temperature rose from room temperature to 150° C. The residual dispersion was transferred under a protective gas into the flask of a rotary evaporator and concentrated to dryness under a pressure falling from ambient pressure to <1 mbar and at a maximum temperature of 170° C. 30 g of a pourable magnesium methylate powder having an average particle size of about 50 μm (evaluation by light microscopy) were obtained.

EXAMPLE 8

Use as a catalyst support for propene polymerization 20 g of the magnesium ethylate obtained in Example 4 were dispersed in 200 ml of absolute ethanol under a dry nitrogen atmosphere using a "high shear" disperser. As a result of the action of the shear forces thus generated, the bulk of the silica coating was detached. After sedimentation for 2 hours, the supernatant, slightly turbid, opalescent phase was decanted. This phase contained the bulk of the silica. The sediment, consisting of spherical magnesium ethylate (average particle diameter 5 μm) was freed from ethanol by distillation and converted by the method described in Published European Application 0 236 082 into a catalyst suitable for propene polymerization. The catalyst proved to be equivalent to the prior art produced with respect to activity and stereospecificity in propene polymerization.

The polymer particles, like the catalyst support particles, had a virtually precise spherical shape with a smooth surface. Particle size analysis (laser measurement) showed a narrow particle size distribution: for an average particle diameter of 152 μm the proportion of particles > 1000 μm was 0.1% (oversize particles), and the proportion of particles < 100 μm was 5.8%.

EXAMPLE 9 COMPARISON EXAMPLE

Spray-drying of carbonized magnesium ethylate solution and use as catalyst support for propene polymerization 1835 g of ethanol and 292 g of magnesium ethylate (standard grain, commercial product from Hüls AG) were introduced into a reactor, fitted with a stirrer, a gas inlet device and a distillation bridge, under a dry nitrogen atmosphere. 194 g of $CO_2$ were passed in over the course of 2 hours, while stirring. A flesh-colored solution of carbonized magnesium ethylate in ethanol was formed. This solution was subjected to spray-drying in a laboratory spray drier (Büchi) using a throughput of 307 ml/hour, a temperature of 190° C. at the spray nozzle and a nitrogen throughput of about 600 liters/hour. The pourable powder obtained thereby consisted of carbonized magnesium ethylate. For decarbonization and in order to remove the residual moisture (ethanol), the powder was subjected to a heat treatment for 2 hours at 180° C. and a pressure of <1 mbar. The average particle diameter was about 5 μm with a highly structured surface (raisin structure). Using the process described in Published European Application 0 236 082, the powder was converted into a catalyst suitable for propene polymerization. The catalyst proved to be equivalent to the prior art product with respect to activity and stereospecificity in propene polymerization. The polymer particles, like the catalyst particles, had a very irregular surface structure. Particle size analysis (laser measurement, sieve analysis) showed a relatively wide particle size distribution: for an average particle diameter of 140 μm the proportion of particles > 1000 μm was 4.7%, and the proportion of particles < 100 μm was 23.5%. The proportion of oversize and undersize particles was thus, for a comparable average particle size of both the catalyst support particle and the polymer particle, considerably greater in the case of the spray-drying process than in the case of the precipitation process according to the present invention.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. The method of preparing an alkaline earth metal compound of the formula $$M(OR^1)_a(OR^2)_b(CO_2)_x$$

wherein M is an alkaline earth metal selected from the group consisting of magnesium, calcium, strontium and barium;

$R^1$ and $R^2$ are identical or different alkyl radicals of 1 to 6 carbon atoms;

$a+b=2$, $0 \leq a \leq 2$, $0 \leq b \leq 2$, and $0 \leq x \leq 2$, having a spherical or spheroid particle form, which comprises the sequential steps of forming said particles from a homogeneous solution consisting of an alkaline earth metal lower alkylate or its carbonized form dissolved in a polar protic solvent, to which only one polar or non-polar aprotic solvent has been added which is miscible with the solution of the alkaline earth metal lower alkylate or its carbonized form but wherein said alkaline earth metal lower alkylated or its carbonized form is only sparsely soluble or insoluble, and distilling off the polar protic solvent.

2. The method of claim 1, wherein said polar protic solvent is a straight-chain or branched alkanol of 1 to 6 carbon atoms.

3. The method of claim 1, wherein said polar or non-polar aprotic solvent is an ether of ethylene glycol, an aliphatic, cyclic or aromatic hydrocarbon, a chlorination product of these hydrocarbons, a tetraalkoxysilane, or an alkyl-, dialkyl- or trialkylalkoxysilane.

4. The method of claim 1, wherein ethanol, methanol, propanol, isopropanol or butanol is used as the polar protic solvent, and xylene, diethylene glycol dimethyl ether, tetraethoxysilane or tetramethoxysilane is used as the polar or non-polar aprotic solvent.

5. The method of claim 1, wherein said alkaline earth metal lower alkylate is magnesium methylate or magnesium ethylate.

6. The method of claim 1, wherein $CO_2$ is used in order to increase the solubility of the alkaline earth metal alkylate in the polar protic solvent.

7. The method of claim 1, wherein the particle size is controlled by controlling the shear gradient employed for the precipitation or by particle stabilization by means of the addition of pyrogenic silica during the precipitation reaction.

* * * * *